United States Patent [19]
Yukawa et al.

[11] Patent Number: 5,331,396
[45] Date of Patent: Jul. 19, 1994

[54] FOREIGN MATTER DETECTION DEVICE

[75] Inventors: Noriaki Yukawa, Nara; Hideshi Ueda, Higashiosaka; Daisuke Ookawara, Itami, all of Japan

[73] Assignee: Matsushita Electric Industrial Co., Ltd., Osaka, Japan

[21] Appl. No.: 958,572

[22] Filed: Oct. 8, 1992

[30] Foreign Application Priority Data

Oct. 8, 1991 [JP] Japan .................. 3-260043

[51] Int. Cl.⁵ .......................................... G01N 21/88
[52] U.S. Cl. ....................................... 350/237
[58] Field of Search ........................... 356/237

[56] References Cited

U.S. PATENT DOCUMENTS

| | | | |
|---|---|---|---|
| 4,280,420 | 7/1981 | Nishida et al. | 112/103 |
| 4,342,515 | 8/1982 | Akiba et al. | 356/237 |
| 4,568,835 | 2/1986 | Imamura et al. | 250/572 |
| 4,614,427 | 9/1986 | Koizumi et al. | 356/237 |
| 4,669,875 | 6/1987 | Shiba et al. | 356/237 |
| 4,740,079 | 4/1988 | Koizumi et al. | 356/237 |
| 4,886,975 | 12/1989 | Murakami et al. | 250/572 |
| 4,922,308 | 5/1990 | Noguchi et al. | 356/237 |
| 4,952,058 | 8/1990 | Noguchi et al. | 356/237 |
| 5,017,798 | 5/1991 | Murakami et al. | 250/572 |

FOREIGN PATENT DOCUMENTS

| | | |
|---|---|---|
| 52-14477 | 2/1977 | Japan . |
| 52-140384 | 11/1977 | Japan . |
| 54-101389 | 8/1979 | Japan . |
| 56-86340 | 7/1981 | Japan . |
| 56-115945 | 9/1981 | Japan . |
| 59-12341 | 1/1984 | Japan . |
| 59-152625 | 8/1984 | Japan . |
| 60-80745 | 5/1985 | Japan . |
| 60-222756 | 11/1985 | Japan . |
| 60-222757 | 11/1985 | Japan . |
| 61-104242 | 5/1986 | Japan . |
| 61-162738 | 7/1986 | Japan . |
| 61-180128 | 8/1986 | Japan . |
| 61-230048 | 10/1986 | Japan . |
| 62-134647 | 6/1987 | Japan . |
| 64-453 | 1/1989 | Japan . |

OTHER PUBLICATIONS

*Fine Particle Inspectors and Measuring Technology for Microcontamination* (Translation), issued by Hitachi Denshi Enjiniaringu Giho, vol. 1 (1991). (no month).
*Contaminant Detection Method Utilizating Polarization Characteristics of Light Reflected from LSI Pattern* (Translation), issued by Hitachi Denshi Enjiniaringu Giho, vol. 1 (1991). (no month).

Primary Examiner—Richard A. Rosenberger
Attorney, Agent, or Firm—Ratner & Prestia

[57] ABSTRACT

A foreign matter detection device, for detecting a foreign matter on a photomask of transparent material with opaque patterns formed thereon, includes a laser source for emitting an S-polarized laser beam so as to impinge on a first surface of the photomask which reflects a P-polarized laser beam. A light source is provided to illuminate the photomask at an opposed surface to the first surface, from which a light transmits. This reflected P-polarized laser beam and transmitted light enters, through a condenser lens and a deflection plate, into a CCD in which an image representing the condition of the impinged surface is obtained. Since the P-polarized laser beam indicative of the corner edge of the pattern is offset by the transmitted light passing around the same corner edge, the pattern image is obscured and foreign matter is distinguishable in the obtained image.

7 Claims, 5 Drawing Sheets

FOREIGN MATTER DETECTION DEVICE

BACKGROUND OF THE INVENTION

1. Field of the Invention

The present invention relates to a device for detecting a foreign matter on a test piece for use in semiconductor production and, more particularly, on a photomask having a given pattern thereon.

2. Description of the Prior Art

Two important problems faced in improving semiconductor production processes in recent years have been improving product reliability and yields. Most defects found during the initial production processes in large-scale integration semiconductor (LSI and VLSI) device production are caused by foreign matter in the processes. Developing equipment that can detect such foreign matter at high speed and with high reliability is the key to overcoming this production problem.

Most conventional foreign matter detection devices are based on detection of laser scattered light, and are capable of detecting foreign matter with a minimum size of approximately 0.2 μm using devices that scan mirror-finish test pieces. For example, U.S. Pat. No. 4,342,515 issued Aug. 3, 1982, to Akiba et al. (corresponding to the Japanese Laid-open Patent Publication No. 54-101390 published Aug. 9, 1979 (unexamined)). discloses a typical device which makes it possible to distinguish foreign matter from the pattern. Devices that scan test pieces with an imprinted pattern can detect foreign matter with a minimum size of approximately 0.5 μm.

Figure 9A:
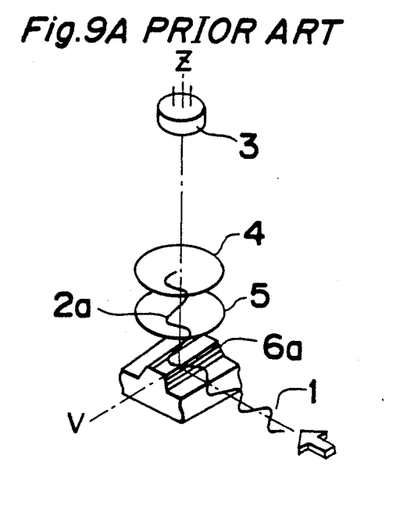
Figure 9B:
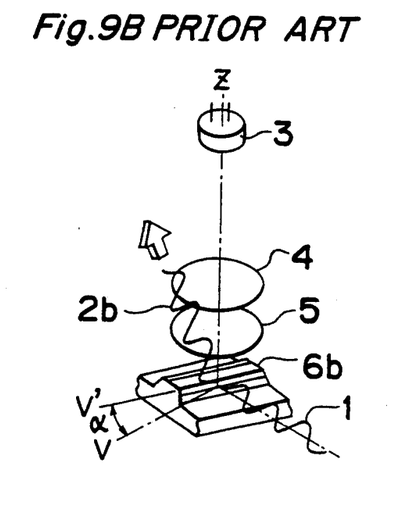
Figure 9C:
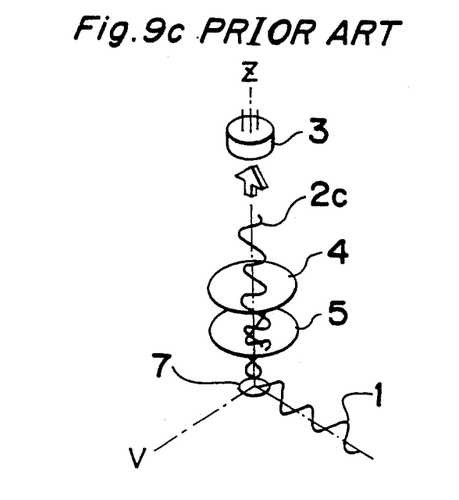

Referring to FIGS. 9A, 9B, and 9C, the operation of a conventional device capable of detecting foreign matter on a patterned test piece is described below. This device works by impinging a S-polarized laser beam 1 on the test piece having a pattern, and detecting differences in the polarization characteristics of scattered laser beams from the pattern edge and foreign matter.

FIG. 9A shows a case in which the S-polarized laser beam 1 is emitted approximately parallel to the upper surface of a photomask 6a having a pattern extending in a direction V, perpendicular to the S-polarized laser beam 1. As a result, there is no change in the polarization of reflected laser beam 2a from the photomask pattern 6a, and it enters into an object lens 5 with the S-polarization. Because a deflector plate 4 is placed to pass the light having a polarization perpendicular to the S-polarization, the reflected laser beam 2a is quenched by the deflector plate 4 and can not reach a detection element 3 such as a photoelectric multiplier.

FIG. 9B shows a case in which the S-polarized laser beam 1 is emitted to a photomask 6b in a manner very similar to that of FIG. 9A, but a pattern of photomask 6b extends in a direction V' having an angle α with respect to the direction V. The reflected laser beam 2b from the pattern of photomask 6b is not incident to the object lens 5, much less the detection element 3, as shown.

FIG. 9C shows a case in which the S-polarized laser beam 1 is emitted to a foreign matter 7 in a manner very similar to those of FIGS. 9A and 9B. When the laser beam 1 is impinged on the foreign matter 7, a P-polarized laser beam 2c having a polarization perpendicular to that of S-polarization is further reflected therefrom in addition to the S-polarized laser beam. Because the deflector plate 4 passes only the light having a polarization perpendicular to the S-polarization as described before, only the reflected laser beam 2c therefore can pass into the detection element 3 through the object lens 5 and deflection plate 4. Thus, the information with respect to the polarization in reflected laser beams 2a and 2c can be utilized to detect the foreign matter 7 on the photomasks 6a and 6b.

In general, when a laser beam is impinged on a test piece such as a photomask, non-directional scattered light is reflected from foreign matter on the photomask, and directional scattered light is reflected from the pattern formed on the photomask, specifically from the edge of the circuit pattern formed by a light shielded material such as chromium. Therefore, the foreign matter can be detected by utilizing the deflection or similar factors to shut the directional scattered light caused by the pattern edges.

However, in the conventional device with the above described configuration, when the laser beam 1 is impinged on a surface of the photomask, some portion of the laser beam 1 is reflected by the impinged surface of the photomask and the remaining portion thereof is incident to the photomask through the impinged surface. This reflected or incident laser beam reaches the detection element 3 after repeated reflecting or scattering inside the device, causing the element 3 to produce a photoelectric signal indicating that scattered light from foreign matter was received even though there is not actually any foreign matter present. This is particularly a problem when extremely minute foreign matter must be detected, or when the incidence angle of the deflected laser beam is offset from the horizontal. Thus, the conventional devices can not detect foreign matter with precision and reliability enough to satisfy the requirement of the present semiconductor production field.

Furthermore, in the conventional foreign matter detection device, it is impossible to recognize the shape and content or type of the foreign matter. This is because a photomultiplier can only process the photoelectric level of the reflected laser beam and can not produce the scanned area's image based on such a reflected laser beam. Therefore, it is necessary to move the laser beam 1 on the scanning area of the photomask to obtain the information with respect to the positional relationship between the detected foreign matter and the photomask, requiring substantial scanning time and a complicated mechanism for scanning.

Still furthermore, in the conventional foreign matter detection device, the incident angle of the S-polarized laser beam with respect to the surface of the test piece must be controlled within 2° to 30°. This is because when the incident angle is less than 2°, the pattern hinders the laser beam from impinging the neighboring pattern (such patterns are placed very closely together). Also when the incident angle is greater than 30°, the scanning area on the test piece impinged by the laser beam becomes too small.

SUMMARY OF THE INVENTION

The object of the present invention is therefore to provide a foreign matter detection device which solves these problems.

The present invention has been developed with a view to substantially solving the above described disadvantages and has for its essential object to provide an improved foreign matter detection device.

In order to achieve the aforementioned objective, a foreign matter detection device, for detecting a foreign matter on a test piece made of a first optically transmissible material with patterns made of a second optically transmissible material which can transmit the light less than the first transmissible material formed thereon, comprises a first illumination means for emitting a coherent light having a first predetermined diameter to impinge on a first surface of the test piece at a predetermined incidence angle with respect to the first surface and to produce a reflected coherent light reflected from the first surface, the coherent light being polarized in a first direction parallel to a surface of the test piece, the reflected coherent light being polarized at a second direction perpendicular to the first direction; a second illumination means for emitting an illumination light to illuminate a second surface opposed to the first surface of the test piece and to produce a transmitted light transmitted from the first surface; and an image forming means for forming a first image of the first surface based on the reflected coherent light and the transmitted light, whereby the reflected coherent light reflected from the pattern edge is added with the transmitted light passing through the pattern such that the light intensity distribution at the pattern edge is smoothed and that at the foreign matter is enhanced.

BRIEF DESCRIPTION OF THE DRAWINGS

These and other objects and features of the present invention will become clear from the following description taken in conjunction with the preferred embodiment thereof with reference to the accompanying drawings throughout which like parts are designated by like reference numerals, and in which.

DETAILED DESCRIPTION OF THE PREFERRED EMBODIMENT

Figure 1:
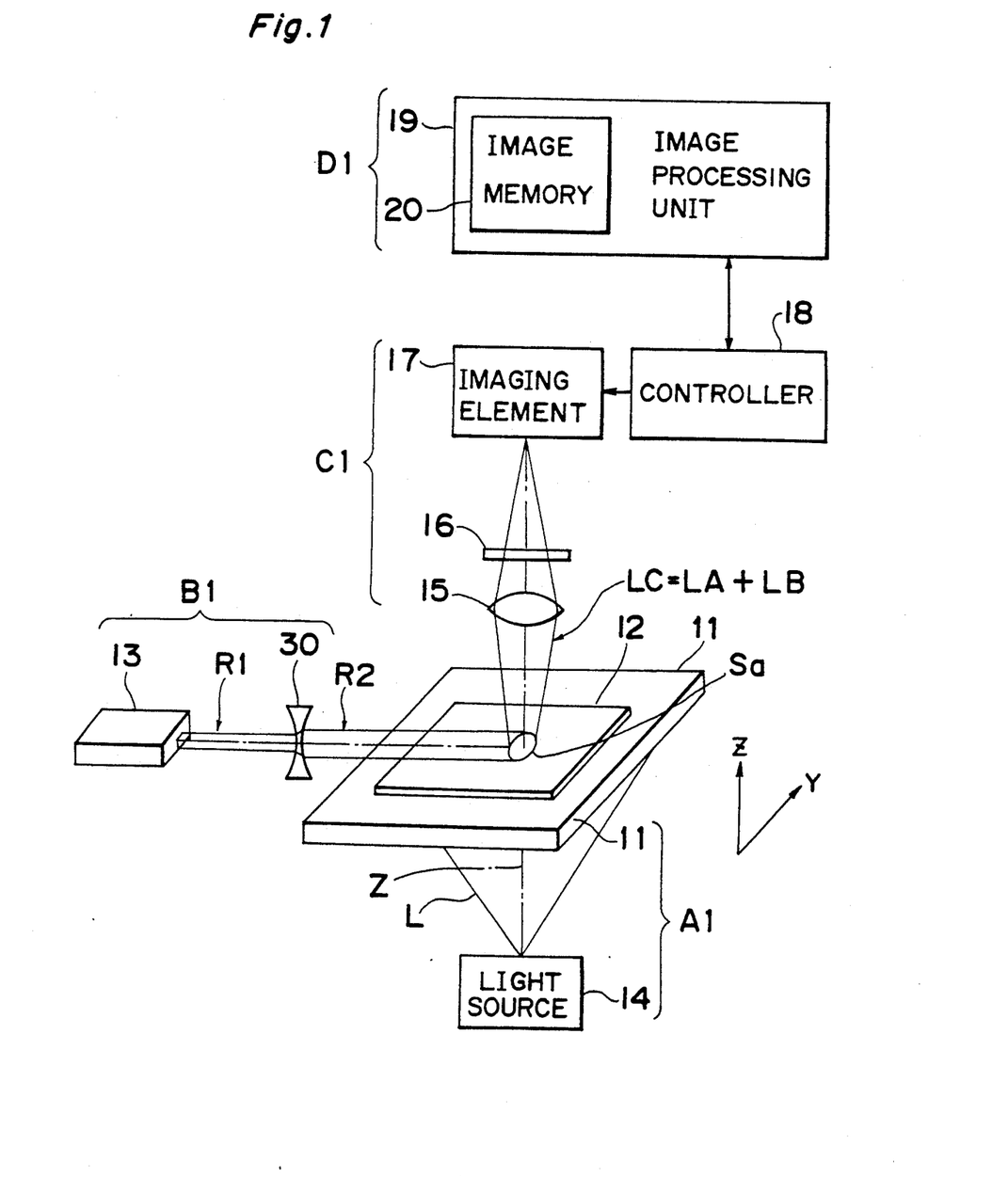
FIG. 1 is a schematic view of a foreign matter detection device according to the present invention.

Referring to FIG. 1, a foreign matter detection device according to a preferred embodiment of the present invention is shown. The foreign matter detection device comprises an illumination light source unit A1 for illuminating a test piece 12, a coherent light source unit B1 for impinging the coherent light on the test piece 12 surface at a predetermined incidence angle with respect to an upper surface of test piece 12, a detection unit C1, and a processing unit D1. As a test piece 12, a photomask is substantially made of transparent material with a plurality of patterns made of an opaque material such as chromium.

The illumination light source unit A1 includes a sample stand 11 made of a transparent material for supporting the test piece thereon and a light source 14 for emitting a light along an axis Z for illuminating the test piece through the sample stand 11. The axis Z is preferably perpendicular to the sample stand 11 surface.

Figure 5A:
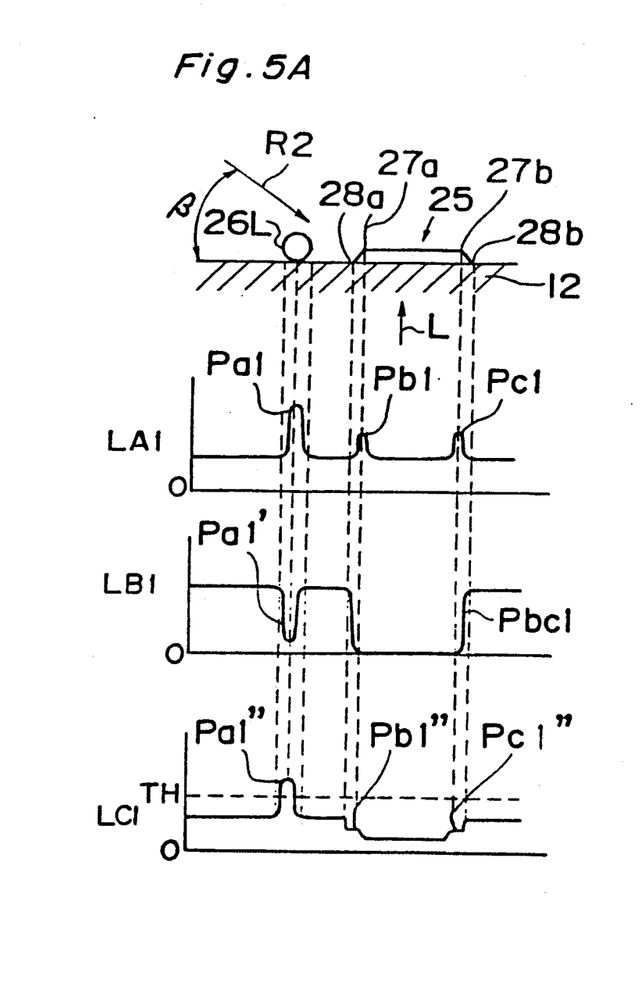
FIG. 5A is a graph showing one-dimensional light intensity distributions on the examination area with a larger foreign matter thereon, each resulting from the laser beam, the of illumination light, and the combination of laser beam and illumination light, respectively.

The coherent light source unit B1 includes a laser source 13 for emitting a first S-polarized coherent laser beam R1 having a first predetermined diameter and a divergent lens 30 for expanding the first S-polarized laser beam R1 to produce a second S-polarized laser beam R2 having a second predetermined diameter. The S-polarized laser beam has a vibration of vectors in a direction parallel to the test piece surface. The laser beam R2 impinges on the test piece 12 surface at a predetermined incidence angle $\beta$, as shown in FIG. 5A, so that the impinged laser beam R2 forms an oval spot Sa on the surface of the test piece 12 which is also illuminated by the illumination light source unit A1.

The detection unit C1 includes a condenser lens 15 for condensing the light coming from the spot Sa, a deflection plate 16, and an imaging element 17 wherein the deflection plate 16 is provided to cut off the S-polarized light. The condenser lens 15 and imaging element 17 have optical axes each in alignment with the axis Z. The deflection plate 16 is provided between the condenser lens 15 and the imaging element 17 with its main plane perpendicular to the axis Z. The deflection plate 16 has a size large enough to extend across the condensed light. The imaging element 17, such as a charge-coupled device (CCD), receives the condensed light, through the deflection plate, from the spot Sa and obtains an image of the test piece 12 surface.

The image processing unit D1 includes a controller 18 and an image processing unit 19, wherein the controller 18 is electrically connected with the imaging element 17 and also to the image processing unit 19. The image processing unit 19 includes an image memory 20 therein.

It is needless to say that the coherent light to be impinged on the test piece is not limited to the laser beam but other type of coherent light can be used.

In operation, the presence and absence of a foreign matter on the test piece 12 is detected. The test piece 12 is illuminated simultaneously by the second laser beam R2 and by the light L.

Figure 2:
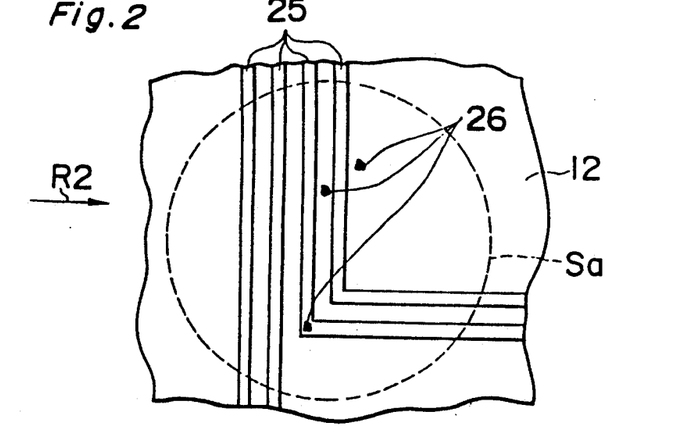
FIG. 2 is a plan view of examination area on the test piece to be scanned by the foreign matter detection device shown in FIG. 1.

Referring to FIG. 2, an upper surface of the photomask 12 where the spot Sa is formed by the second laser beam R2 is shown. To inspect the entire surface of the test piece 12, the spot Sa is scanned by a suitable scanning means. According to the example shown in FIG. 2, some patterns 25 formed on the photomask 12 extend perpendicularly and others extend parallel to the second laser beam R2. Also, according to the example shown in FIG. 2, three foreign matters 26 are present. The second laser beam R2 forms the spot Sa having a diameter of about 1 mm so that an area covered by the spot of 1 mm diameter can be detected by a single spot beam shooting.

Figure 3:
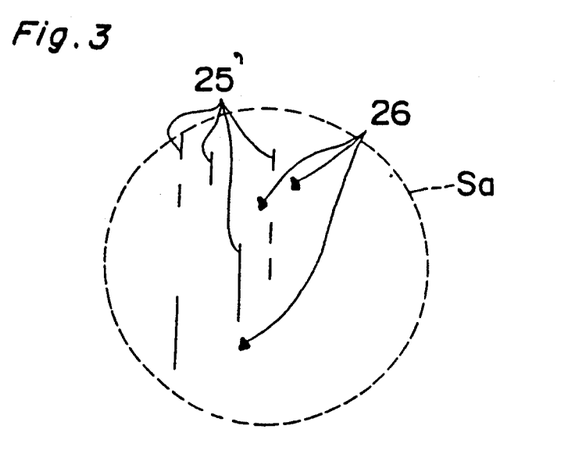
FIG. 3 is an image obtained by the foreign matter detection device shown in FIG. 2 when a laser beam is impinged on the examination area.

Referring to FIG. 3, an image of spot Sa obtained by the imaging element 17 when the second laser beam R2 is used is shown. When the S-polarized laser beam R2 is reflected at the edges of the pattern extending perpendicular to the laser beam R2, the S-polarized laser beam is changed to a P-polarized laser beam LA after reflection. The P-polarized laser beam has a vibration of vectors in a direction perpendicular to the test piece surface. In other words, the P-polarization and S-polarization are crossing each other at a right angle. This P-polarized laser beam LA reaches, through the condenser lens 15 and the deflection plate 16, the imaging element 17 which obtains an image of the spot Sa, as shown in FIG. 3.

For convenience of illustration, the foreign matters 26 are shown black in the figures, but in fact simply have brighter images than the background, because the image density of the foreign matters 26 is greater than that of the background. Thin and shining lines 25' represent edges of the patterns 25. The lines 25' are separated because some edges of patterns 25 are rounded to scatter the second laser beam R2. The scattering at the edge of the pattern becomes more manifest as the angle between the horizontal plane of the test piece 12 surface and the laser beam R2 becomes greater. This is an important factor for determining the incidence angle of the laser beam R2 to examine the test piece surface.

Figure 4:
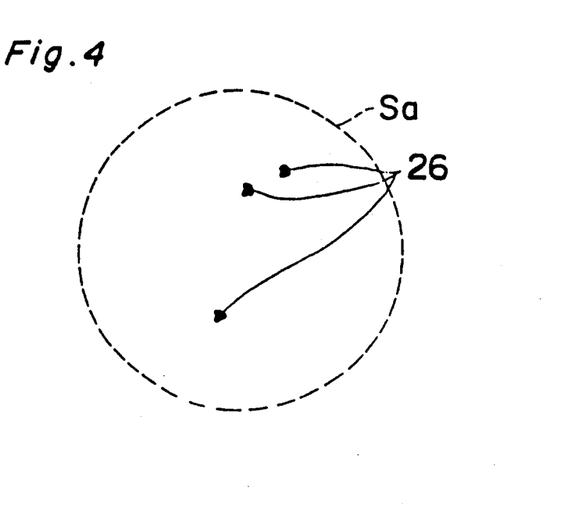
FIG. 4 is an image obtained by the foreign matter detection device shown in FIG. 3 when an illumination light is further impinged on the examination area.

Referring to FIG. 4, an image of spot Sa obtained by the imaging element 17 when the illumination light L, in addition to the second laser beam R2, is applied to the photomask 12 is shown. The light L transmitted through the sample stand 11 enters the photomask 12. The light L transmitted through the photomask 12, particularly at the spot Sa is applied to the imaging element 17 through the condenser lens 15 and deflection plate 16. The transmitted light LB carries the optical information of the photomask 12 such as the presence of the patterns and foreign matters. The P-polarized reflected laser LA and transmitted light LB is mixed and combined as a combined image light LC which carries the optical information indicative of the surface condition of the spot area Sa of the photomask 12. The combined image light LC reaches, through the condenser lens 15 and the deflection plate 16, the imaging element 17 which obtains an image shown in FIG. 4.

The lines 25' indicating the pattern edge 25 are eliminated in FIG. 4. This is because the low image density portion of the transmitted light LB indicative of the opaque patterns counterbalances the high image density portion of the P-polarized reflected laser beam LA indicative of pattern corner 25'. This is further described with reference to the light intensity distribution described in FIGS. 5A and 5B, herebelow.

Referring to FIG. 5A, the light intensity distribution of the image obtained by the imaging element 17 when a larger foreign matter 26L is placed near the mask pattern 25 on the photomask 12 is shown. The pattern thickness is about 0.05 to 0.1 μm, and the minimum size of foreign matter 26L to be detected on a photomask for a 64M DRAM device is approximately 0.5 μm. The second laser beam R2 impinges on the upper surface of the photomask 12 from a side with an incidence angle $\beta$, as shown in FIG. 5A.

The waveform LA1 in the first graph represents the light intensity distribution of the P-polarized laser beam reflected from the photomask 12 surface. Since the top surface of the photomask 12 is flat and constant, the laser beam reflected therefrom is low and constant, forming a flat background level.

Since the pattern 25 is formed substantially in a trapezoid shaped in cross section, the density level of laser beam LA reflected from the pattern 25 increases at both sides 28a and 28b, with a peak level obtained at the edge portions 27a and 27b, thus causing two peaks Pb1 and Pc1.

Since the foreign matter 26L is large and has indefinite configuration, the foreign matter 26L scatters and reflects the P-polarized laser beam LA at the upper hemisphere thereof such that the density level of the laser beam is greatest at the top of the hemisphere and becomes smaller at positions apart from the top, causing a peak Pa1 as shown.

It is to be noted that line LA1 shows the light intensity distribution obtained by the foreign matter detection device according to the prior art, in which only the S-polarized laser beam R2 is applied for detection of the foreign matter.

The line LB1 in the second graph represents the light intensity distribution of the transmitted light L only. Since the photomask 12 is made of transparent material, the light passes through the portion with no foreign matter or no pattern, forming a flat background level as shown.

Since the foreign matter 26L is made of various material in a indefinite configuration, the light L is out at the foreign matter 26L. Thus the density level of the transmitted light LB through the foreign matter 26L becomes low and has a valley around the center portion, causing a negative peak Pa1' as shown.

Since the pattern 25 is formed by an opaque material, the light is also cut at pattern 25. Therefore, the density level of the transmitted light LB is low when the pattern 25 is present, causing a trapezoid shaped valley Pbc1 as shown. Although the pattern 25 is covered with an opaque material such as chromium in this embodiment, any other transparent material less optically transmissible than the material of photomask 12 can be employed. This is because such less transmissible material can also cause a trapezoid shaped valley having a bottom level lower than the background in the transmitted light LB.

The line LC1 in the third graph represents the light intensity distribution of the combined image light LC. In the combined image light LC where the laser beam LA and transmitted light LB are mixed, the peaks Pa1 and Pa1' are added to form a peak Pa1" having a level in proportion to the size of the foreign matter 26L. Furthermore, peaks Pb1 and Pc1 are added with the valley Pbc1 to produce small peaks Pb1" and Pc1" indicative of the edges of pattern 25.

The image obtained on the imaging element 17 is further processed for the detection of the foreign matter as described. The image processing unit 19 sets a threshold TH at a level above the peaks Pb1" and Pc1" but below the peak Pa1", as shown by a dotted line TH in FIG. 5A. Thus, the pattern edges 25' are completely eliminated from the image and only the foreign matters 26 can be distinguished, as shown in FIG. 4.

Furthermore, using an imaging element such as a CCD makes it possible to determine the position, shape, and area of the foreign matter. Scanning the laser beam R2 on the photomask 12 which is essential to the conventional devices to determine the position of the foreign matter is not required at all. The material or type of the foreign matter can also be determined by more specifically investigating the density distribution. When a color imaging screen is used, the type can be even more clearly specified by the color information. This is a feature that cannot be obtained using a photoelectric multiplier for the optical detection means as in conventional processes.

Figure 5B:
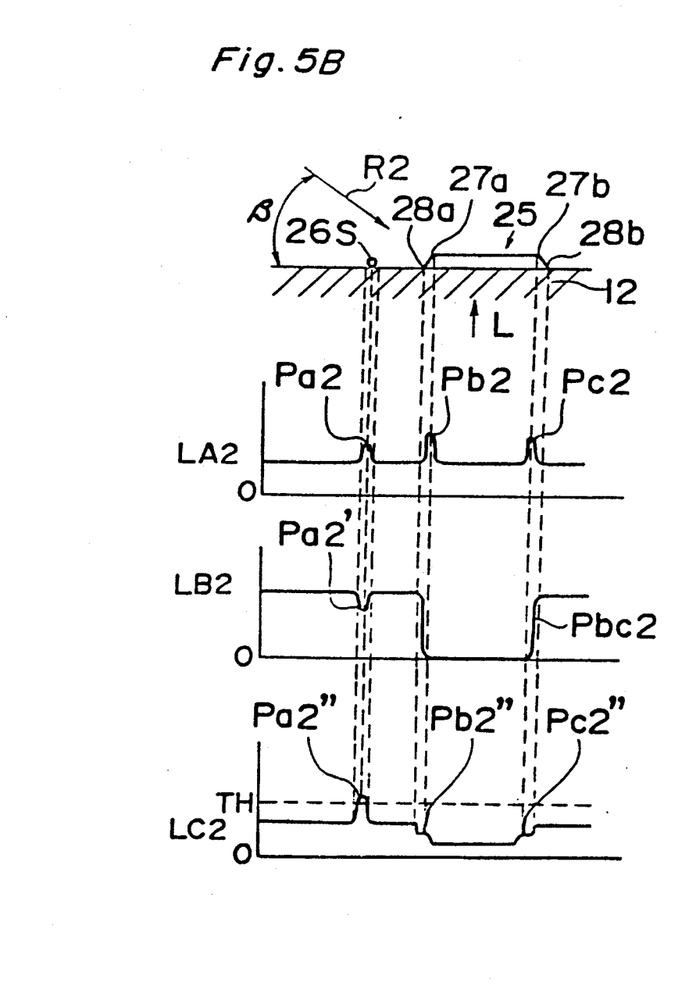
FIG. 5B is a graph showing one-dimensional light intensity distributions on the examination area with a smaller foreign matter thereon, each resulting from the laser beam, the illumination light, and the combination of laser beam and illumination light, respectively.

Referring to FIG. 5B, the light intensity distribution of the image obtained by the imaging element 17 very similar to that shown in FIG. 5A is shown. The larger foreign matter 26L in FIG. 5A is replaced with a smaller foreign matter 26S in FIG. 5B.

In line LA2, the density level of laser beam LA shows two peaks Pb2 and Pc2, and a peak Pa2, representing the pattern 25 edges 27a and 27b, and the foreign matter 26S, respectively. Since the foreign matter 26S is quite small, the foreign matter 26S reflects the light laser beam R2 less than the pattern 25 reflects, causing the level of peak Pa2 to fall below the peaks Pb2 and Pc2. In this case, it is very difficult to recognize the foreign matter 26S because the image density of the foreign matter 26S is less than that of the background and is smaller than that indicative of the edges of pattern 25.

However, by adding the transmitted light LB to the test piece 12, the light intensity distribution of the transmitted light LB shows a small negative peak Pa2' representing the foreign matter 26S and a trapezoid shaped valley Pbc2 representing the pattern 25, as shown.

In the line LC2, the combined light intensity distribution of the lines LA2 and LB2 is shown. Adding peaks Pa2 and Pa2' forms a peak Pa2'', representing the foreign matter 26s. Adding peaks Pb2 and Pc2, and valley Pbc2 forms the peaks Pb2'' and Pc2'', representing the edges of the pattern 25. The peaks of light intensity distribution in reflected laser beam LA are counterbalanced by the transmitted light LB, so that peak Pa2'' has a level greater than peaks Pb2'' and Pc2''. Therefore, it is possible to distinguish the foreign matter 26S by setting a threshold TH above the peaks Pb2'' and Pc2'' and below Pa2''. Thus, by applying the transmitted light L in addition to the laser beam R2, even a foreign matter too small to detect by the laser beam R2 only can be detected.

Before the process of threshold setting, noise signals are eliminated, and the target pixel is compared with surrounding pixels. When FIGS. 3 and 4 are compared, it is obvious that the effect of the pattern is suppressed by the transmitted light LB, and the ability to detect foreign matter on the subject is improved. In methods using a conventional photomultiplier as the imaging element 17, it is difficult to completely eliminate the influence of the pattern because only the reflected laser beam from the test piece is utilized for detecting the foreign matter.

Referring to FIGS. 6, 7A, 7B, and 8, image processing of the obtained image data according to the present invention is described hereinbelow.

Figure 6:
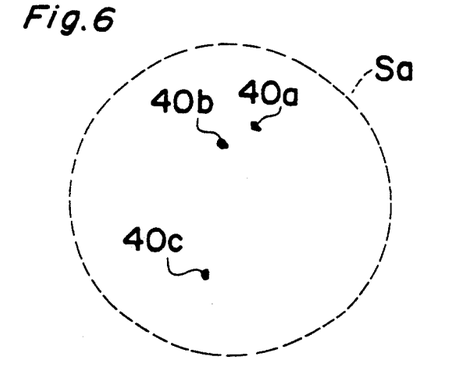
FIG. 6 is an image obtained from the examination area with a plurality of foreign matters each located at different levels, resulting from the combination of the laser beam and illumination light.

As shown in FIG. 6, there are three foreign matters 40a, 40b, 40c which are distinguishable in the image obtained by the same manner as described with reference to FIG. 4. This image is stored by an image memory 20 incorporated in the image processing unit 19. The view of the upper surface of the photomask 12 on the spot Sa, in this case, is very similar to that shown in FIG. 2. The foreign matter 40c is located on the mask pattern 25 formed on the photomask 12 and foreign matters 40a and 40b are located on places other than the mask pattern 25 as shown in the figure.

Figure 7A:
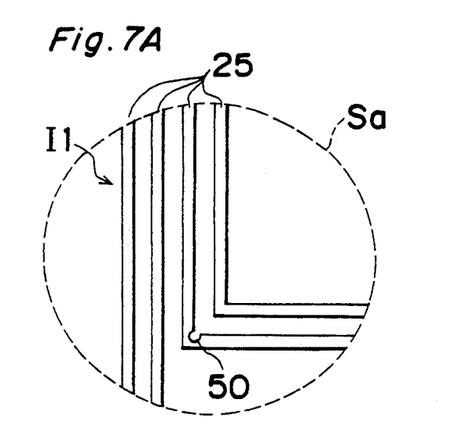
FIG. 7A is an image obtained by applying a pattern recognition process to the image of FIG. 6.

As shown in FIG. 7A, the view of the spot Sa obtained by the imaging element 17 processed by the processing unit 19 is such that the pattern 25 is also recognized based on all pixels with a density value below a predetermined threshold value TH, as described with reference to FIG. 5A. Thus, a first binary image I1 is obtained. In the first binary image I1, an area 50 can not be recognized as part of the pattern 25 because of foreign matter 40c thereon. The first binary image I1 is further processed by the processing unit 19 so that enlarging and reducing processes, well known to the skilled person in the art of image processing, are applied to the image I1 to remove foreign matter in the pattern, resulting in a second binary image I2.

Figure 7B:
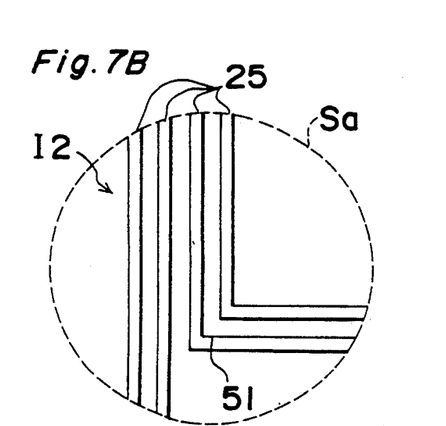
FIG. 7B is an image obtained by applying an image enlargement and reduction process to the image of FIG. 7A.

As shown in FIG. 7B, thus, the area 51 which corresponds to area 50 in the first binary image I1 can now be recognized as a part of the pattern 25 in the second binary image I2, because of the enlarging/reducing process.

Figure 8:
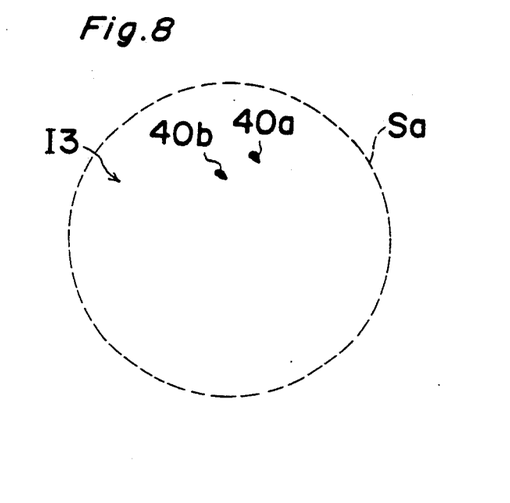
FIG. 8 is an image obtained by comparing the image of FIG. 6 with the image of FIG. 7B, and FIGS. 9A, 9B, and 9C are schematic views of a foreign matter detection device according to the prior art.

The image processing unit 19 compares the second binary image I2 with the image shown in FIG. 6 stored in the image memory 20 to obtain an image I3 shown in FIG. 8 from which foreign matter 40c on the pattern 25 has been removed, leaving just the foreign matter 40a and 40b that are not on any pattern line. These objects 40a and 40b represent foreign matter that could be transferred to the wafer when the pattern is exposed, and must therefore be removed. While conventional methods require manual visual confirmation to determine whether the detected foreign matter is on a pattern line or not, the device according to the present invention automatically discriminates such foreign matter.

With the devices described above, it is difficult to separate only the foreign matter or only the pattern from an input image containing both foreign matter and pattern lines when even higher precision detection is required. To correct this, an image obtained by applying only the deflected laser beam R2 and an image obtained by applying only the illumination light L are prepared. Foreign matter detection and pattern detection are performed by combining these two images. Other than separating the imaging process, the configuration and processing method are the same as described above. This method also makes it possible to increase the foreign matter discrimination capability of the device.

It is to be noted that in the preferred embodiment of the present invention, the intensity of the laser beams R1 and R2 and the illumination light L need only be sufficient to detect foreign matter and to avoid the influence of the pattern. In addition, the wavelength of the laser beams only needs to be sufficient to react with the imaging element. The spot diameter also only needs to be large enough to illuminate an area equivalent to one field of the imaging element. The illumination light source also only needs to be sufficient to satisfy processing requirements. Any degree of incidence angle $\alpha$ of the laser beam R2 must only be sufficient to capture minute foreign matter, and to obtain an image whereby the pattern can be counterbalanced by image processing. The density gradations and threshold values of the image processing routine must also only be sufficient to enable foreign matter and pattern recognition. The content or type of the foreign matter does not influence the detection capability of the device according to the present invention. The enlargement and reduction processes are only specified as being sufficient to reproduce the pattern, and the method of discriminating foreign matter on the pattern is also not defined.

As is clear from the above description, the foreign matter detection device according to the present invention can detect foreign matter with high precision and reliability. In experiments using devices and the methods of the present invention, it was found that the area covered by one pixel in the imaging element can be made between four and nine times larger than the actual size of the detected foreign matter. This is because a laser beam, a strong coherent light source, is emitted to the subject, causing the scattered light from the foreign matter to spread over an area larger than the size of the foreign matter, and the imaging element responds to this larger area.

As a result, by combining efficient laser emissions and high speed image processing, a 100×100 mm photomask can be scanned at one time for detection of foreign matter as small as 0.5 μm with processing completed in approximately four minutes. One pixel can cover a 2.0×2.0 mm area on the photomask. In addition, the processing speed can be increased even more by combining multiple devices. The device can also be easily modified to scan for foreign matter of different sizes by simply changing the magnification of the condenser lens.

Because an imaging element is used as the detecting element, unlike conventional devices, it is also possible to easily recognize the shape and content or type of the foreign matter. Demand for such a device has been high, and the invention is expected to provide significant real benefits.

The effect of foreign matter on semiconductor production processes is great, and there has been strong demand for a device capable of detecting foreign matter with high speed and high reliability. The potential effect of the present invention is therefore believed to be extremely high.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A foreign matter detection device for detecting a foreign matter on a test piece made of a first optically transmissible material with patterns made of a second optically transmissible material which can transmit the light less than said first transmissible material formed thereon, said device comprising:

a first illumination means for emitting a coherent light having a first predetermined diameter to impinge on a first surface of said test piece at a predetermined incidence angle with respect to said first surface and to produce a reflected coherent light reflected from said first surface, said coherent light being polarized in a first direction parallel to said first surface of said test piece, said reflected coherent light being polarized in a second direction perpendicular to said first direction;

a second illumination means for emitting an illumination light to illuminate a second surface opposed to said first surface of said test piece and to produce a transmitted light transmitted from said first surface; and an image forming means for forming a first image of said first surface based on said reflected coherent light and said transmitted light, whereby said reflected coherent light reflected from said pattern edge is added with said transmitted light passing through said pattern such that the light intensity distribution at said pattern edge is smoothed and that at said foreign matter is enhanced.

2. A foreign matter detection device as claimed in claim 1, further comprising an expansion means for expanding said coherent light to have a second predetermined diameter for impinging a widened area of said first surface of said test piece.

3. A foreign matter detection device as claimed in claim 1, wherein said image forming means comprises an imaging element adapted to recognize the shape and type of said foreign matter captured in said first image.

4. A foreign matter detection device as claimed in claim 3, wherein said imaging element is a charge-coupled device.

5. A foreign matter detection device as claimed in claim 1, further comprising:

a first image processing means for producing a second image detecting only said pattern by enhancing the pattern image included in said first image, said detected pattern being incomplete because of the foreign matter on said pattern;

a second image processing means for producing a third image including a compensated image of said pattern by image processing; and a third image processing means for producing a fourth image with said foreign matter on said pattern eliminated therefrom by comparing said first image with said third image.

6. A foreign matter detection device as claimed in claim 5, further comprising an image memory means for storing said first, second, third, and fourth images.

7. A foreign matter detection device as claimed in claim 5, wherein said first, second, and third image processing means and said memory means are integrally incorporated.

* * * * *

UNITED STATES PATENT AND TRADEMARK OFFICE
CERTIFICATE OF CORRECTION

PATENT NO.   : 5,331,396
DATED        : July 19, 1994
INVENTOR(S)  : Noriaki Yukawa et al.

It is certified that error appears in the above-identified patent and that said Letters Patent is hereby corrected as shown below:

Cover Page, [75] the third inventor's last name should be --Ohgawara--.

Column 3, line 49, before "laser" insert --the--.

Column 3, line 48, before "illumination" delete --of--.

Signed and Sealed this

Sixth Day of December, 1994

Attest:

BRUCE LEHMAN

Attesting Officer          Commissioner of Patents and Trademarks